(12) United States Patent
Tischer

(10) Patent No.: US 6,930,086 B2
(45) Date of Patent: Aug. 16, 2005

(54) DIGLYCOSYLATED ERYTHROPOIETIN

(75) Inventor: Wilhelm Tischer, Peissenberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 82 days.

(21) Appl. No.: 10/241,356

(22) Filed: Sep. 11, 2002

(65) Prior Publication Data

US 2003/0077753 A1 Apr. 24, 2003

(30) Foreign Application Priority Data

Sep. 25, 2001 (EP) .............................................. 01122555

(51) Int. Cl.$^7$ .......................... C07K 1/00; C07K 14/00; A61K 38/00; C12N 15/00
(52) U.S. Cl. .......................... 514/2; 435/69.1; 435/69.4; 514/814; 530/395; 530/333; 930/10; 930/90
(58) Field of Search .............................. 435/69.1, 69.4; 514/2, 814; 530/395, 333; 930/10, 90

(56) References Cited

FOREIGN PATENT DOCUMENTS

| EP | 0 409 113 | 1/1991 |
|---|---|---|
| EP | 0 410 246 | 1/1991 |
| EP | 411 678 | 2/1991 |
| EP | 640 619 | 3/1995 |
| WO | WO 97/09996 | 3/1997 |
| WO | WO 00 32772 | 6/2000 |
| WO | WO 01/02017 | 1/2001 |

OTHER PUBLICATIONS

Felix et al., ACS Symp. Ser. 680, pp. 218–238 (1997).
Broudy et al., Arch. Biochem. Biophys., 265, pp. 329–336 (1988).
Lai et al., J. Biol. Chem., 261, pp. 3116–3121 (1986).
Nimtz et al., Eur. J. Biochem, 213, pp. 39–56 (1993).
Sasaki et al., Biochemistry, 27, pp. 8618–8626 (1988).
Delorme et al., Biochemistry, 31, pp. 9871–9876 (1992).
Fibi et al., Blood, 85, pp. 1229–1236 (1995).
Veronese, Biomaterials, 22, pp. 405–417 (2001).
Cointe Didier, et al., Glycobiology, vol. 10, No. 5, pp. 511–519 (2000).
Yamaguchi, K., et al., Journal of Biological Chemistry, American Society of Biological Chemists, Baltimore, MD, vol. 266, No. 30, pp. 20434–20439 (1991).
Dube, S., et al., Journal of Biological Chemistry, Society of Biological Chemists, Baltimore, MD, vol. 263, No. 33, pp. 17516–17521 (1988).

*Primary Examiner*—Jon Weber
*Assistant Examiner*—Holly Schnizer
(74) *Attorney, Agent, or Firm*—George W. Johnston; Patricia S. Rocha-Tramaloni

(57) ABSTRACT

This invention is directed to an erythropoietin mutein having in vivo biological activity for causing bone marrow cells to increase production of reticulocytes and red blood cells, in that the mutein is N-glycosylated at Asn38 and Asn83 but not N-glycosylated at Asn24. Such muteins have improved pharmaceutical properties.

44 Claims, No Drawings

SEQUENCE LISTING

<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
         50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp
            165
```

<210> SEQ ID NO 2
<211> LENGTH: 166
<212> TYPE: PRT
<213> ORGANISM: Homo sapiens

<400> SEQUENCE: 2

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
         50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140
```

```
-continued

Tyr Ser Asn Phe Leu Arg Gly Lys Leu Lys Leu Tyr Thr Gly Glu Ala
145                 150                 155                 160

Cys Arg Thr Gly Asp Arg
                165
```

DIGLYCOSYLATED ERYTHROPOIETIN

FIELD OF THE INVENTION

The invention relates to new variants of erythropoietin that are diglycosylated, methods for the production and use, as well as pharmaceutical compositions thereof.

BACKGROUND OF THE INVENTION

Erythropoiesis is the production of red blood cells which occurs to offset cell destruction. Erythropoiesis is a controlled physiological mechanism that enables sufficient red blood cells to be available for proper tissue oxygenation. Naturally occurring human erythropoietin (hEPO) is a glycoprotein containing 165 amino acids that is produced in the kidney and is the humoral plasma factor which stimulates red blood cell production. Human EPO stimulates the division and differentiation of committed erythroid progenitors in the bone marrow. Human EPO exerts its biological activity by binding to receptors on erythroid precursors. Naturally occurring human erythropoietin is an acidic glycoprotein present in low concentrations in plasma to stimulate replacement of red blood cells which are lost through ageing.

Erythropoietin has been manufactured biosynthetically using recombinant DNA technology (Egrie, J. C., et al., Immunobiol. 72 (1986) 213–224) and is the product of a cloned human EPO gene inserted into and expressed in the ovarian tissue cells of the Chinese hamster (CHO cells). Naturally occurring human EPO is first translated to a 166 aa containing polypeptide chain with arginine 166. In a postranslational modification, arginine 166 is cleaved by a carboxypeptidase. The primary structure of human EPO (165 aa and 166 aa) is shown in SEQ ID NO:1 and SEQ ID NO:2. There are two disulfide bridges between Cys7–Cys161 and Cys29–Cys33. The molecular weight of the polypeptide chain of human EPO without the sugar moieties is 18,236 Da. In the intact EPO molecule, approximately 40% of the molecular weight is accounted for by the carbohydrate groups (Sasaki, H., et al., J. Biol. Chem. 262 (1987) 12059–12076).

Because erythropoietin is essential in red blood cell formation, it is useful in the treatment of blood disorders characterized by low or defective red blood cell production. Clinically, EPO is used in the treatment of various ailments, for example, anemia in chronic renal failure patients (CRF) and in AIDS and cancer patients undergoing chemotherapy (Danna, R. P., et al., In: M B, Garnick, ed. Erythropoietin in Clinical Applications—An International Perspective. New York, N.Y.: Marcel Dekker; 1990, pp. 301–324). However, the bioavailability of currently available protein therapeutics such as erythropoietin is limited by their short plasma half-life and susceptibility to protease degradation. These shortcomings prevent them from attaining maximum clinical potency.

Modifications of the amino acid sequence of EPO have been disclosed, for example, in a number of references including U.S. Pat. No. 4,835,260; WO 94/25055; WO 94/24160; WO 94/02611; WO 95/05465.

Both human urinary derived erythropoietin and recombinant erythropoietin (expressed in mammalian cells) contain three N-linked and one O-linked oligosaccharide chains which together comprise about 40% of the total molecular weight of the glycoprotein. N-linked glycosylation occurs at asparagine residues located at positions 24, 38 and 83 while O-linked glycosylation occurs at a serine residue located at position 126 (Lai, et al., J. Biol. Chem. 261 (1986) 3116; Broudy, V. C., et al., Arch. Biochem. Biophys. 265 (1988) 329). The oligosaccharide chains have been shown to be modified with terminal sialic acid residues. Enzymatic treatment of glycosylated erythropoietin to remove all sialic acid residues results in a loss of in vivo activity but does not affect in vitro activity (Lowy et al., Nature 185 (1960) 102; Goldwasser, E., et al. J. Biol. Chem. 249 (1974) 4202–4206). This behavior has been explained by rapid clearance of asialoerythropoietin from circulation upon interaction with the hepatic asialoglycoprotein binding protein (Morrell et al., J. Biol. Chem. 243 (1968) 155; Briggs, D. W., et al., Am. J. Physiol. 227 (1974) 1385–1388; Ashwell, G., and Kawasaki, T., Methods Enzymol. 50 (1978) 287–288). Thus, erythropoietin possesses in vivo biological activity only when it is sialylated to avoid its binding by the hepatic binding protein.

The role of the other components in the oligosaccharide chains of erythropoietin is not well defined. It has been shown that partially diglycosylated erythropoietin has greatly reduced in vivo activity compared to the glycosylated form but does retain in vitro activity (Dordal, M. S., et al., Endocrinology 116 (1985) 2293–2299). In another study, however, the removal of N-linked or O-linked oligosaccharide chains singly or together by mutagenesis of asparagine or serine residues that are glycosylation sites sharply reduces in vitro activity of the altered erythropoietin that is produced in mammalian cells (Dube, S., et al., J. Biol. Chem. 263 (1988) 17516–17521).

Oligonucleotide-directed mutagenesis has been used to prepare structural mutants of EPO lacking specific sites for glycosylation (Yamaguchi, K., et al., J. Biol. Chem. 266 (1991) 20434–20439; and Higuchi, M., et al., J. Biol. Chem. 267 (1992) 7703–7709). Cloning and expression of non-glycosylated EPO in *E.coli* is described by Lee-Huang, S., Proc. Natl. Acad. Sci. USA 61 (1984) 2708–2712; and in U.S. Pat. No. 5,641,663.

EP 0 640 619 relates to analogs of human erythropoietin comprising an amino acid sequence which includes at least one additional site for glycosylation. The added sites for glycosylation may result in a greater number of carbohydrate chains, and higher sialic acid content, than human erythropoietin. Erythropoietin analogs comprising amino acid sequences which include the rearrangement of at least one site for glycosylation are also provided. Analogs comprising an addition of one or more amino acids to the carboxy terminal end of erythropoietin wherein the addition provides at least one glycosylation site are also included.

PEGylation of glycosylated EPO is described in WO 01/02017. Such molecules show an improved biological activity. WO 00/32772 and Francis, G. E., et al., Int. J. Hem. 68 (1988) 1–18, describe polyethylene glycol- modified non-glycosylated EPO. The molecules of WO 00/32772 are additionally modified at positions 166. Such molecules are described as not causing a significant increase in hematocrite. The PEG-polymer portion consists of 1–5 polymer chains. WO 00/32772 suggests to control the degree and site of PEGylation by lowering the pH and reducing the PEG: amine ratio. Reactions run at pH 7 and 1.5:1 molar ratio of PEG-aldehyde: amine groups, preferentially react with the N-terminal α-amino group.

In spite of the numerous modifications that are known for EPO, there still exists a need for further EPO muteins with modified properties, especially with modified clearance and simple, reproducible methods for its production.

SUMMARY OF THE INVENTION

The invention provides a new class of EPO muteins. The EPO muteins according to the invention have the in vivo biological activity of causing bone marrow cells to increase production of reticulocytes and red blood cells.

The invention provides an erythropoietin mutein which has retained the potential N-glycosylation sites at Asn24, Asn38, Asn83, is N-glycosylated at Asn38 and Asn83 but is not N-glycosylated at Asn24 and is preferably linked at the N-terminal amino group and/or the ε-amino group of Lys20 to poly(ethylene glycol) group(s) (PEG), preferably to alkoxypoly(ethylene glycol) group(s), more preferably to lower methoxypoly(ethylene glycol) group(s).

The muteins of this invention have the same uses as EPO. In particular, the muteins of this invention are useful to treat patients by stimulating the division and differentiation of committed erythroid progenitors in the bone marrow. In the same way EPO is used to treat patients.

The invention also provides an aqueous composition comprising an erythropoietin mutein having N-glycosylation sites at Asn38 and Asn83 but not at Asn24, and a pharmaceutically acceptable buffer thereof.

In yet another embodiment, this invention provides a pharmaceutical composition comprising an erythropoietin mutein or an aqueous composition as referred to above.

The present invention also includes a method for making erythropoietin muteins according to the invention, which comprises the production of a glycosylated EPO fragment consisting of the amino acids 26–165 (EPO 26–165) and subsequent chemically linking or fusing of said fragment with a non-glycosylated but preferably PEGylated EPO fragment consisting of the amino acids 1–28 (EPO 1–28).

This invention is also directed to a method of treating a disease relating to anemia in chronic renal failure patients or to AIDS and the treatment of cancer patients undergoing chemotherapy comprising administering to a patient in need thereof a therapeutically effective amount of a mutein or composition as referred to above.

DETAILED DESCRIPTION OF THE INVENTION

The term "erythropoietin" (EPO) refers to a protein having the sequence SEQ ID NO:1 or SEQ ID NO:2, or a protein or polypeptide substantially homologous thereto, whose biological properties relate to the stimulation of red blood cell production and the stimulation of the division and differentiation of committed erythroid progenitors in the bone marrow.

The term "substantially homologous" means that a particular subject sequence, for example, a mutant sequence, varies from a reference sequence by one to five substitutions, deletions, or additions, the net effect of which does not result in an adverse functional dissimilarity between the reference and subject sequences. However, as mentioned above, the potential glycosylation sites Asn24, Asn38 and Asn83 are retained.

Human EPO has one o-glycosylation site (at Ser126 of SEQ ID NO:1) and three N-glycosylation sites (at Asn24, Asn38 and Asn83 of SEQ ID NO:1). The glycosyl residues at these sites are sialylated and are important for the in vivo half-life and subsequently for the efficacy of EPO. Elimination of glycosylation sites Asn24 results in an EPO mutein with improved in vivo efficacy. However, such EPO muteins can only be produced according to the state of the art by replacement of Asn24 by another amino acid which cannot be glycosylated. Therefore, these muteins differ from naturally occurring EPO by having an amino acid modified at a sensible position of the sequence. Such EPO muteins with modified amino acid sequence and modified glycosylation are described, for example, by Nimtz, M., et al., Eur. J. Biochem. 213 (1993) 39–56; Sasaki, H., et al., Biochemistry 27 (1988) 8618–8626; Delorme, C., et al., Biochemistry 31 (1992) 9871–9876; Fibi, M. R., et al., Blood 85 (1995) 1229–1236; and WO 99/11781 (see also EP 0 411 678; Takeuchi, M., et al., Proc. Natl. Acad. Sci. USA 86 (1989) 7819–7822; EP 0 427 189; EP 0 409 113; Dube, S., et al., J. Biol. Chem. 263 (1988) 17516–17521; Yamaguchi, K., et al., J. Biol. Chem. 266 (1991) 20434–20439; EP 0 640 619; and Fibi, M. R., et al., Applied Microbiol. Biotechnol 35 (1991) 622–630).

Therefore, glycosylation to Asn24 can be prevented only by deleting, modifying or substituting this amino acid. Erythropoietin muteins which have retained the amino acids Asn24, Asn38 and Asn83, but are only glycosylated at Asn38 and Asn83, and not glycosylated at Asn24, are not known in the art and there is nothing in the art to provide guidance on how to produce such molecules.

The present invention provides a simple method for the production of EPO muteins which retain glycosylation, preferably natural glycosylation, in the C-terminal part of the molecule beginning with Cys29, being not glycosylated in the N-terminal part up to Gly28, whereby, in addition, said N-terminal part can be modified very easily and in a broad manner, if desired. Such a modification is, for example, a reproducible and defined attachment of side chains such as polyethylene glycols.

The term "N-terminal EPO fragment" or "EPO 1–28" refers to an EPO fragment having amino acids 1–28 of SEQ ID NO:1 or SEQ ID NO:2. As mentioned above, the term also comprises fragments with slight modifications in amino acid sequence (up to about two exchanges, additions, deletions) as long as the pharmaceutical properties of EPO in the ligated molecule are not adversely affected and as long as Asn24 is retained and Gly28 is retained at the C-terminus of the sequence of the fragment.

The term "C-terminal EPO fragment" or "EPO 29–165" refers to an EPO fragment having amino acids 29–165 of SEQ ID NO:1 or of amino acids 29–166 of SEQ ID NO:2. As mentioned above, the term also comprises fragments with slight modifications in amino acid sequence (up to about three exchanges, additions, deletions) as long as the pharmaceutical properties of EPO in the ligated molecule are not adversely affected and as long as Asn38 and Asn83 are retained and Cys29 is retained as N-terminal amino acid of said fragment.

According to the invention, the C-terminal part of erythropoietin beginning with Cys29 is produced recombinantly in eukaryotic cells, whereby Asn38 and Asn83 are glycosylated, while the N-terminal part from the beginning to Gly28 is synthesized in vitro by chemical reaction.

Therefore the invention provides a method for making an EPO mutant comprising chemically linking an N-terminal EPO fragment consisting of amino acids 1–28 of EPO having retained Asn24 and Gly28 with a C-terminal EPO fragment consisting of amino acids 29–165 or 166 of EPO being glycosylated at Asn38 and Asn83 and having retained Cys29 between Gly28 and Cys 29, and then isolating the EPO mutein.

Recombinant C-terminal EPO fragment may be prepared via expression in eukaryotic cells, for example in CHO, BHK or HeLa cell lines by recombinant DNA technology or by endogenous gene activation, that is, the erythropoietin glycoprotein is expressed by endogenous gene activation. The preferred erythropoietin muteins according to the invention are based on the sequence of human EPO. More preferably, the human EPO has the amino acid sequence set out in SEQ ID NO:1 or SEQ ID NO:2, most preferably, the human EPO having the amino acid sequence set out in SEQ ID NO:1.

The C-terminal EPO fragment is produced preferably in CHO cells in the same manner as full-length EPO is produced, or preferably also by endogenous gene activation of human cells according to WO 99/05268 and EP 1 037 821.

The N-terminal EPO fragment can be synthesized by using stepwise solid-phase methods, cleaved from the resin and deprotected. It can be purified by chromatography, e.g., by high-performance liquid chromatography and characterized by ion-spray mass spectrometry as described, e.g., in Schnoelzer, M., et al., Int. J. Pept. Protein Res. 40 (1992) 180–193; Dawson, P. E., et al., Science 266 (1994) 776–779; and Schnoelzer et al., G. G. Fields (ed.), Solid Phase Peptide Synthesis, Methods Enzymology 289 (1977), see whole volume. At the C-terminus, the fragment preferably contains a thiocarboxyester group for binding with Cys29 of the C-terminal fragment.

The ligation of the N-terminal and C-terminal EPO fragments can be performed by native chemical ligation in a simple manner as long as the C-terminal fragment has an amino-terminal cysteine residue, which preferably is Cys29 (Dawson, P. E., et al., Science 266 (1994) 776–779). According to this principle, the N-terminal fragment contains a thioester at the α-carboxyl group and undergoes nucleophilic attack by the side-chain of the cysteine residue at the amino terminus of the C-terminal fragment. The initial thioester ligation product undergoes rapid intramolecular reaction yielding a product with a native peptide bond at the ligation site. Such methods for chemical ligation of peptides are reviewed in Dawson, P. E., and Kent, S. B. H., Annual Review of Biochemistry 69 (2000) 923–960.

The N-terminal EPO fragment and the C-terminal EPO fragment were preferably solubilized during ligation in a denaturing solution such as guanidine hydrochloride or urea and ligated according to Dawson, P. E., et al., Science 266 (1994) 776–779, or Dawson, P. E., et al., J. Am. Chem. Soc., 119 (1997) 4325–4329.

The purification of the ligated EPO mutein is performed by conventional methods such as affinity chromatography, size-exclusion chromatography and ion-exchange chromatography.

The term "PEGylation" means a covalent linkage of a (polyethylene) glycol residue at the N-terminus of the polypeptide and/or lysine 20. PEGylation of proteins is widely known in the state of the art and reviewed by, for example, Veronese, F. M., Biomaterials 22 (2001) 405–417. PEG can be linked using different functional groups and polyethylene glycols with different molecular weight, linear and branched PEGs as well as different linking groups (see also Francis, G. E., et al., Int. J. Hematol. 68 (1998) 1–18; Delgado, C., et al., Crit. Rev. Ther. Drug Carrier Systems 9 (1992) 249–304).

PEGylation of the N-terminal fragment can be performed in aqueous solution with PEGylation reagents as described, for example, in WO 00/44785, preferably using NHS-activated linear or branched PEG molecules of a molecular weight between 5 and 40 kDa. PEGylation can also be performed at the solid phase according to Lu, Y., et al., Reactive Polymers 22 (1994) 221–229.

These methods result in an N-terminal EPO fragment which is PEGylated at the ε-amino group of Lys20 and/or at the N-terminal amino group Selective PEGylation at the N-terminal amino acid can be performed according to Felix, A. M., et al., ACS Symp. Ser. 680 (Poly(ethylene glycol)) (1997) 218–238. Selective N-terminal PEGylation are achieved during solid-phase synthesis by coupling of a $N^\alpha$-PEGylated amino acid derivative to the N-1 terminal amino acid of the peptide chain. Side chain PEGylation are performed during solid-phase synthesis by coupling of $N^\epsilon$-PEGylated lysine derivatives to the growing chain. Combined N-terminal and side chain PEGylation are proceeded either as described above within solid-phase synthesis or by solution phase synthesis by applying activated PEG reagents to the amino deprotected peptide.

Suitable PEG derivatives are activated PEG molecules with a preferred average molecular weight of from about 5 to about 40 kDa, more preferably from about 20 to about 40 kDa, and most preferably about 30 kDa. The PEG derivatives can be linear or branched PEGs. A wide variety of PEG derivatives suitable for use in the preparation of PEG-protein and PEG-peptide conjugates can be obtained from Shearwater Polymers (Huntsville, Ala., U.S.A.

Activated PEG derivatives are known in the art and are described in, for example, Morpurgo, M., et al., J. Bioconj. Chem. 7 (1996) 363–368, for PEG-vinylsulfone. Linear chain and branched chain PEG species are suitable for the preparation of the PEGylated fragments. Examples of reactive PEG reagents are iodo-acetyl-methoxy-PEG and methoxy-PEG-vinylsulfone (m is preferably an integer from about 450 to about 900 and R is lower alkyl, linear or branched, having one to six carbon atoms such as methyl, ethyl, isopropyl, etc. whereby methyl is preferred):

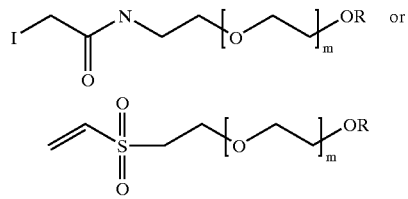

The use of these iodo-activated substances is known in the art and described, e.g., by Hermanson, G. T., in Bioconjugate Techniques, Academic Press, San Diego (1996) p. 147–148.

Most preferably, the PEG species are activated by N-hydroxy succinimide ester using (alkoxy-PEG-N-hydroxysuccinimide, such as methoxy-PEG-N-hydroxysuccinimide (MW 30000; Shearwater Polymers, Inc.)), wherein R and m are as defined above.

The term "lower alkoxy" refers to an alkyl ether group in which the term 'alkyl' means a straight-chain or branched-chain alkyl group containing a maximum of 4 carbon atoms, such as methoxy, ethoxy, n-propoxy and the like, and preferably methoxy.

The further purification of the PEGylated N-terminal fragments, including the separation of mono- or di-PEGylated species, are performed by methods known in the art, e.g., column chromatography.

Further, the present invention refers to an aqueous composition and a pharmaceutical composition comprising an EPO mutein or a composition as defined above and a pharmaceutically acceptable excipient, such as a buffer, and to the use of an EPO mutein or a composition as defined above for the preparation of pharmaceutical compositions for the treatment or prophylaxis of diseases correlated with anemia in chronic renal failure patients (CRF), AIDS and for the treatment of cancer patients undergoing chemotherapy. In addition, the invention refers to a method for the prophylactic and/or therapeutic treatment of disorders involving anemia in chronic renal failure patients (CRF), AIDS and cancer patients undergoing chemotherapy comprising the step of administering to a patient a composition as defined above in a therapeutically effective amount.

The term "therapeutically effective amount" is that amount of the erythropoietin mutein according to the invention necessary for the in vivo biological activity of causing bone marrow cells to increase production of reticulocytes and red blood cells. The exact amount of erythropoietin mutein is a matter of preference subject to such factors as the exact type of condition being treated, the condition of the patient being treated, as well as the other ingredients in the composition. The pharmaceutical compositions containing the erythropoietin muteins are formulated at a strength effective for administration by various means to a human patient experiencing blood disorders characterized by low or defective red blood cell production. Average therapeutically effective amounts of the erythropoietin glycoprotein product may vary and in particular should be based upon the recommendations and prescription of a qualified physician.

Further, the invention refers to EPO muteins and compositions as defined above whenever prepared by the processes described above and to EPO muteins and compositions as defined above for the treatment of diseases which are associated with anemia in chronic renal failure patients (CRF), AIDS and cancer patients undergoing chemotherapy.

The EPO fragments and EPO muteins according to the invention can be purified according to processes known in the art.

In EP-A 0 267 678, an ion exchange chromatography on S-Sepharose, a preparative reverse phase HPLC on a C8 column and a gel filtration chromatography are described for the purification of EPO. In this connection, the gel filtration chromatography step are replaced by ion exchange chromatography on S-Sepharose fast flow. It is also proposed that a dye chromatography on a Blue Trisacryl column be carried out before the ion exchange chromatography. A process for the purification of recombinant EPO is also described by Nobuo, I., et al., J. Biochem. 107 (1990) 352–359. In this process, EPO is treated however with a solution of Tween®20, phenylmethylsulfonyl fluoride, ethylmaleimide, pepstatin A, copper sulfate and oxamic acid prior to the purification steps.

The specific activity of EPO or EPO muteins in accordance with this invention can be determined by various assays known in the art. The biological activity of the purified EPO proteins of this invention are such that administration of the EPO protein by injection to human patients results in bone marrow cells increasing production of reticulocytes and red blood cells compared to non-injected or control groups of subjects. The biological activity of the EPO muteins, or fragments thereof, obtained and purified in accordance with this invention can be tested by methods according to Pharm. Europa Spec. Issue Erythropoietin BRP Bio 1997(2).

Another biological assay for determining the activity of EPO, the normocythaemic mouse assay, is described in Example 5.

The erythropoietin mutein prepared in accordance with this invention may be prepared in pharmaceutical compositions suitable for injection with a pharmaceutically acceptable carrier or vehicle by methods known in the art. For example, appropriate compositions have been described in WO 97/09996, WO 97/40850, WO 98/58660, and WO 99/07401. Among the preferred pharmaceutically acceptable carriers for formulating the products of the invention include human serum albumin and human plasma proteins. The compounds of the present invention may be formulated in 10 mM sodium/potassium phosphate buffer at pH 7 containing a tonicity agent, e.g., 132 mM sodium chloride. Optionally, the pharmaceutical composition may contain a preservative. The pharmaceutical composition may contain different amounts of erythropoietin, e.g., 10 to 1000 µg/ml, e.g., 50 µg to 400 µg.

Administration of the erythropoietin glycoprotein products of the present invention results in red blood cell formation in humans. Therefore, administration of the erythropoietin glycoprotein products replenishes this EPO protein, which is important for the production of red blood cells. The pharmaceutical compositions containing the erythropoietin glycoprotein products may be formulated at a strength effective for administration by various means to a human patient experiencing blood disorders, characterized by low or defective red blood cell production, either alone or as part condition or disease. The pharmaceutical compositions may be administered by injection such as by subcutaneous or intravenous injection. Average quantities of the erythropoietin glycoprotein product may vary and in particular should be based upon the recommendations and prescription of a qualified physician. The exact amount of conjugate is a matter of preference subject to such factors as the exact type of condition being treated, the condition of the patient being treated, as well as the other ingredients in the composition. For example, 0.01 to 10 µg per kg body weight, preferably 0.1 to 1 µg per kg body weight, may be administered on a regular basis, e.g., once weekly.

Throughout this application, various publications have been referenced. The disclosures in these publications are incorporated herein by reference in order to describe more fully the state of the art.

The following examples, references and sequence listing are provided to aid the understanding of the present invention, the true scope of which is set forth in the appended claims. It is understood that modifications can be made in the procedures set forth without departing from the spirit of the invention.

EXAMPLE 1

Production of PEGylated EPO (1–28): Synthesis of $N^{\alpha}$-PEG-$CH_2$—CO-(Lys(PEG-$CH_2$—CO)$^{20}$)-EPO (1–28)αCOSBzl and isolation of mono-PEGylated fractions Peptide was synthesized by using stepwise solid-phase methods, cleaved from the resin and deprotected, purified by high performance liquid chromatography and characterized by ion-spray mass spectrometry as described in literature (see Schnolzer, M., et al., Int. J. Pept. Protein Res. 40 (1992) 180; Schnölzer, P. M., et al., G. G. Fields, ed., Solid-Phase Peptide Synthesis, Meth. Enzymol. 289 (1997), whole volume), wherein for the formation of the C-terminal benzyl thioester the route of Lu, W., et al., J. Am. Chem. Soc., 118 (1996) 8518–8523 was followed.

1.1 Synthesis of PEG-$CH_2$—CO—NHS mPEG-$CH_2$—COOH—($CH_3$—(O—$CH_2$—$CH_2$)$_n$—O—$CH_2$—COOH) was activated with N-hydroxy-succinimide as described by Lu, Y. A., Int. J. Pept. Protein Res. 43 (1994) 127–138. Ethylenoxide repeating units were in the range of n≈110 to give a molecular weight of 5000 (PEG$_{5000}$), n≈440 (PEG$_{20k}$) or n≈880 (PEG$_{40k}$).

1.2 Synthesis of EPO(1–28)αCOSBzl

The N-terminal peptide was prepared with stepwise solid-phase synthesis according to Lu, W., et al., J. Am. Chem. Soc. 118 (1996) 8518–8523. BOC-Gly-(thioester linker)-amino methyl-resin was used for stepwise attachment of amino acids. The received peptide was deprotected and cleaved from the resin. Benzyl bromide was added to prepare the thioester which was then purified by HPLC. Thioester containing fractions were pooled and purified by HPLC.

1.3 PEGylation of EPO(1–28)αCOSBzl

PEG-CH$_2$—CO—NHS was added to N-acylate the peptide at the α-NH$_2$ of N-terminal alanine and at the ε-NH$_2$ of lysine at position 20. The mono- and di-PEGylated EPO (1–28) thioesters were separated and purified by HPLC and lyophilized.

EXAMPLE 2

PEGylation of EPO (1–28) with Bifunctional Reagents a) Covalent Linking of Thiol Groups This example discloses the process in determining the reaction conditions for the covalent linking of thiol groups to the fragment. To determine the conditions, different amounts of a reagent containing a blocked thiol group. In this case, SATA (succinimidyl acetylthioacetate) or SATP (succinimidyl acetylthiopropionate) (dissolved in DMSO at 10 mg/ml) was added to a solution of the fragment EPO (1–28)αCOSBzl, and then to 1 ml of 5 mg/ml fragment in 10 mM potassium phosphate, 50 mM NaCl, pH 7.3. The reaction was stirred for about 30 minutes (25° C.) and stopped by addition of 1 M lysine solution at 10 mM. Excess amounts of SATA and/or SATP were removed by dialysis against 10 mM potassium phosphate, 50 mM NaCl and 2 mM EDTA, pH 6.2. After removal of the protecting acetyl group with hydroxylamine, the number of thiol groups covalently linked to the fragment was determined photometrically with dithiodipyridine according to the method described by Grasetti, D. R. and Murray, J. F., in J. Appl. Biochem. Biotechnol. 119 (1967) 41–49.

b) PEGylation of Activated EPO (1–28)

380 mg methoxy-PEG-maleimide (MW 30,000; Shearwater Polymers, Inc., Huntsville (Ala., USA)) was dissolved in a solution containing 95 mg activated EPO (4.5 mg/ml in 10 mM potassium phosphate, 50 mM NaCl, 2 mM EDTA, pH 6.2). The resulting molar ratio between activated fragment and methoxy-PEG-maleimide in the solution was 1:4. By addition of 1 M aqueous hydroxylamine solution at 30 mM, pH 6.2 to the above solution, the covalently linked blocked thiol groups of activated fragment were de-blocked. The resulting activated fragment in the reaction mixture of the solution contained free thiol (—SH) groups. De-blocking of the thiol groups was followed immediately by the coupling reaction between the activated fragment now containing free thiol (—SH) groups and methoxy-PEG-maleimide for 90 minutes (stirring, 25° C.). The coupling reaction was stopped by addition of 0.2 M aqueous cysteine solution at 2 mM to the reaction mixture. After 30 minutes excess free thiol groups of the activated fragment which did not react with methoxy-PEG-maleimide were blocked by addition of a 0.5 M N-methylmaleimide solution in DMSO to reach a concentration of 5 mM. After 30 minutes, the resulting reaction mixture now containing PEGylated fragment was purified by ion exchange chromatography and dialyzed against 10 mM potassium phosphate, pH 7.5 for ≧15 hours.

EXAMPLE 3

Recombinant Production of EPO (29–165)

EPO (29–165) was prepared in accordance with Example 1 of WO 99/05268.

Harvesting and Cell Separation:

A batch refeed process was used, i.e., when the desired cell density was reached, approx. 80% of the culture was harvested. The remaining culture was replenished with fresh culture medium and cultivated until the next harvest. One production run consists of a maximum of 10 subsequent harvests: 9 partial harvests and 1 overall harvest at the end of fermentation. Harvesting takes place every 3–4 days.

The harvest volume was transferred into a cooled vessel. The cells were removed by centrifugation or filtration and discarded. The fragment containing supernatant of the centrifugation step was in-line filtered and collected in a second cooled vessel. Each harvest was processed separately during purification.

EXAMPLE 4

Ligation and Isolation

Equimolar amounts of both PEG-EPO (1–28) COSBzl prepared according to Examples 1 and 2 and EPO (29–165) were solubilized at about 6 mg/ml in 0.1 M phosphate buffer. 6 M guanidine-HCl at pH 7.5. 3% thiophenol and 1% benzyl mercaptan (by vol.) were added, as well as excess DTT to keep the protein reduced and ligated for about 36 hours until completion. Excess reagents were then removed by ion exchange chromatography. Protein refolding was achieved by adjusting the buffer and pH to about 1 mg/ml protein concentration with 6 M guanidine HCl and dilution to about 0.2 mg/ml. The ligation product was purified according to Example 1 of WO 01/02017.

EXAMPLE 5

In vivo Activity of PEGylated EPO Determined by the Normocythaemic Mouse Assay

PEG-EPO, unmodified EPO and buffer solution were administered to mice. The results show the superior activity and the prolonged half life of the PEGylated EPO species in regard to unmodified EPO indicated by the significantly increased amounts of reticulocytes and the shift of the reticulocytes count maximum using the same dose per mouse.

The normocythaemic mouse bioassay is known in the art (Pharm. Europa Spec. Issue Erythropoietin BRP Bio 1997 (2)) and a method in the monography of erythropoietin of Ph. Eur. BRP. The samples were diluted with BSA-PBS. Normal healthy mice, 7–15 weeks old, were administered s.c. 0.2 ml of PEGylated EPO as described in Example 4. Over a period of 4 days starting 72 hours after the administration, blood was drawn by puncture of the tail vein and diluted such that 1 μl of blood was present in 1 ml of an 0.15 μmol acridine orange staining solution. The staining time was 3 to 10 minutes. The reticulocyte counts were carried out microfluorometrically in a flow cytometer by analysis of the red fluorescence histogram (per 30,000 blood cells analyzed). Each investigated group consisted of 5 mice per day, and the mice were bled only once.

What is claimed is:

1. An erythropoietin protein comprising two glycosylated asparagines at positions 38 and 83 and an unglycosylated asparagine at position 24, wherein the amino acid positions are according to the amino acid sequence of SEQ ID NO:1 or SEQ ID NO:2.

2. The erythropoietin protein according to claim 1, wherein the N-terminal amino group is linked to lower alkoxypoly(ethylene glycol) group(s).

3. The erythropoietin protein according to claim 2, wherein the average molecular weight of each poly(ethylene glycol) moiety is from about 5 kilodaltons to about 40 kilodaltons.

4. The erythropoietin protein according to claim 2, wherein the average molecular weight of each poly(ethylene glycol) moiety is about 30 kilodaltons.

5. The erythropoietin protein of claim 2 wherein the ε-amino group of Lys20 is linked to lower alkoxypoly(ethylene glycol) group(s).

6. The erythropoietin protein according to claim 2, wherein the poly(ethylene glycol) moieties are capped by a methoxy group.

7. The erythropoietin protein according to claim 1, wherein the ε-amino group of Lys20 is linked to lower alkoxypoly(ethylene glycol) group(s).

8. The erythropoietin protein according to claim 7, wherein the average molecular weight of each poly(ethylene glycol) moiety is from about 5 kilodaltons to about 40 kilodaltons.

9. The erythropoietin protein according to claim 7, wherein the average molecular weight of each poly(ethylene glycol) moiety is about 30 kilodaltons.

10. The erythropoietin protein of claim 7, wherein the poly(ethylene glycol) moieties are capped by a methoxy group.

11. The erythropoietin protein of claim 1, wherein the amino acid sequence comprises SEQ ID NO:1 or SEQ ID NO:2.

12. A pharmaceutical composition comprising the erythropoietin protein according to claim 1 and a pharmaceutical acceptable carrier.

13. A method of treating anemia in chronic renal failure patients comprising administering to a patient in need thereof a therapeutically effective amount of the erythropoietin protein according to claim 1.

14. A method of treating anemia in AIDS patients and cancer patients undergoing chemotherapy comprising administering to a patient in need thereof a therapeutically effective amount of the erythropoietin protein according to claim 1.

15. An aqueous composition comprising an erythropoietin protein comprising, two glycosylated asparagines at positions 38 and 83 and an unglycosylated asparagine at position 24, wherein the amino acid position are according to the amino acid sequence of SEQ ID NO:1 or SEQ ID NO:2 and a pharmaceutically acceptable buffer.

16. The aqueous composition according to claim 15, wherein the N-terminal amino group of the erythropoietin protein is linked to lower alkoxypoly(ethylene glycol) group(s).

17. The aqueous composition according to claim 15, wherein the ε-amino group of Lys20 of the erythropoietin protein is linked to lower alkoxypoly(ethylene glycol) group(s).

18. The aqueous composition of claim 15, further comprising a pharmaceutical acceptable carrier.

19. A method of treating anemia in chronic renal failure patients comprising administering to a patient in need thereof a therapeutically effective amount of the composition according to claim 15.

20. A method of treating anemia in AIDS patients and cancer patients undergoing chemotherapy comprising administering to a patient in need thereof a therapeutically effective amount of the composition according to claim 15.

21. A method of making an erythropoietin protein, comprising chemically linking an N-terminal erythropoietin fragment consisting of amino acids 1–28 of erythropoietin having retained Asn24 and Gly28 with a C-terminal erythropoietin fragment consisting of amino acids 29–165 or 29–166 of erythropoietin being glycosylated at Asn38 and Asn83, and having retained Cys29, said linkage occurring between Gly28 and Cys 29, wherein the amino acid positions are relative to SEQ ID NO:1 or SEQ ID NO:2, and isolating the erythropoietin protein.

22. The method according to claim 21, comprising covalently linking a polyethylene glycol residue to the N-terminal erythropoietin fragment at the N-terminus of the erythropoietin sequence.

23. The method according to claim 21, comprising covalently linking a polyethylene glycol residue to the N-terminal erythropoietin fragment at the lysine 20 of the erythropoietin sequence.

24. The method according to claim 21, comprising producing the N-terminal fragment by chemical synthesis.

25. The method according to claim 21, comprising producing the C-terminal fragment by recombinant gene expression.

26. An erythropoietin comprising a protein, wherein the sequence of the protein varies from the amino-acid sequence of SEQ ID NO:1 or SEQ ID NO:2 by 1–5 substitutions, deletions or additions, and further comprising two glycosylated asparagines at positions 38 and 83 and an unglycosylated asparagine at position 24, wherein the amino acid positions are according to the amino acid sequence of SEQ ID NO:1 or SEQ ID NO:2.

27. The erythropoietin protein according to claim 26, wherein the N-terminal amino group is linked to lower alkoxypoly(ethylene glycol) group(s).

28. The erythropoietin protein according to claim 27, wherein the average molecular weight of each poly(ethylene glycol) moiety is from about 5 kilodaltons to about 40 kilodaltons.

29. The erythropoietin protein according to claim 27, wherein the average molecular weight of each poly(ethylene glycol) moiety is about 30 kilodaltons.

30. The erythropoietin protein of claim 27, wherein the ε-amino group of Lys20 is linked to lower alkoxypoly(ethylene glycol) groups.

31. The erythropoietin protein according to claim 27 wherein the

32. The erythropoietin protein according to claim 26, wherein the ε-amino group of Lys20 is linked to lower alkoxypoly(ethylene glycol) group(s).

33. The erythropoietin protein according to claim 32, wherein the average molecular weight of each poly(ethylene glycol) moiety is from about 5 kilodaltons to about 40 kilodaltons.

34. The erythropoietin protein according to claim 32, wherein the average molecular weight of each poly(ethylene glycol) moiety is from about 30 kilodaltons.

35. The erythropoietin protein of claim 32, wherein the poly(ethylene glycol) moieties are capped by a methoxy group.

36. A pharmaceutical composition comprising a protein according to claim 26 and a pharmaceutical acceptable carrier.

37. A method of treating anemia in chronic renal failure patients comprising administering to a patient in need thereof a therapeutically effective amount of the erythropoietin mutein according to claim 26.

38. A method of treating anemia in AIDS patients and cancer patients undergoing chemotherapy comprising administering to a patient in need thereof a therapeutically effective amount of the erythropoietin mutein according to claim 26.

39. An aqueous composition comprising an erythropoietin a protein, wherein the sequence of the protein varies from the amino acid sequence of SEQ ID NO:1 or SEQ ID NO:2 by 1–5 substitutions, deletions or additions, and further comprising two glycosylated asparagines at positions 38 and 83 and an unglycosylated asparagine at position 24 wherein the amino acid positions are according to the amino acid sequence of SEQ ID NO:1 or SEQ ID NO:2, and a pharmaceutically acceptable buffer.

40. The aqueous composition according to claim 39, wherein the erythropoietin mutein at the N-terminal amino group is linked to lower alkoxypoly(ethylene glycol) group(s).

41. The aqueous composition according to claim 39, wherein the erythropoietin mutein at the ε-amino group of Lys20 is linked to lower alkoxypoly(ethylene glycol) group(s).

42. A composition comprising an aqueous composition according to claim 39 and a pharmaceutical acceptable carrier.

43. A method of treating anemia in chronic renal failure patients comprising administering to a patient in need thereof a therapeutically effective amount of the composition according to claim 39.

44. A method of treating anemia in AIDS patients and cancer patients undergoing chemotherapy comprising administering to a patient in need thereof a therapeutically effective amount of the composition according to claim 39.

* * * * *

UNITED STATES PATENT AND TRADEMARK OFFICE
CERTIFICATE OF CORRECTION

PATENT NO. : 6,930,086 B2
DATED : August 16, 2005
INVENTOR(S) : Wilhelm Tischer

It is certified that error appears in the above-identified patent and that said Letters Patent is hereby corrected as shown below:

Column 15,
Line 27, should read -- 31. The erythropoietin protein according to claim 27 wherein the poly(ethylene glycol) moieties are capped by a methoxy group. --.

Signed and Sealed this

Twenty-eighth Day of February, 2006

JON W. DUDAS
*Director of the United States Patent and Trademark Office*